United States Patent
Orr et al.

(10) Patent No.: US 8,821,563 B2
(45) Date of Patent: Sep. 2, 2014

(54) SYSTEM AND METHOD FOR DEPLOYING AND POSITIONING AN ENDOVASCULAR DEVICE

(75) Inventors: David E. Orr, Piedmont, SC (US); William Kurt Dierking, Louisville, KY (US); Jesper S. Petersen, Holmegaard (DK)

(73) Assignee: Cook Medical Technologies LLC, Bloomington, IN (US)

( * ) Notice: Subject to any disclaimer, the term of this patent is extended or adjusted under 35 U.S.C. 154(b) by 762 days.

(21) Appl. No.: 13/124,518

(22) PCT Filed: Oct. 16, 2009

(86) PCT No.: PCT/US2009/005642
§ 371 (c)(1),
(2), (4) Date: Jul. 18, 2011

(87) PCT Pub. No.: WO2010/044874
PCT Pub. Date: Apr. 22, 2010

(65) Prior Publication Data
US 2011/0270374 A1 Nov. 3, 2011

Related U.S. Application Data

(60) Provisional application No. 61/106,374, filed on Oct. 17, 2008.

(51) Int. Cl.
*A61F 2/06* (2013.01)
*A61F 2/966* (2013.01)
*A61F 2/95* (2013.01)

(52) U.S. Cl.
CPC . *A61F 2/95* (2013.01); *A61F 2/966* (2013.01); *A61F 2002/9511* (2013.01)
USPC .......................................................... 623/1.11

(58) Field of Classification Search
CPC ........... A61F 2/00; A61F 2/01; A61F 2/2427; A61F 2/243; A61F 2/2439; A61F 2/95; A61F 2/954; A61F 2/962

USPC ............ 623/1.11, 1.23, 2.11, 23.72; 606/200, 606/213
See application file for complete search history.

(56) References Cited

U.S. PATENT DOCUMENTS

| 5,151,105 A | 9/1992 | Kwan-Gett ..................... 623/1 |
| 6,027,520 A | 2/2000 | Tsugita et al. ................ 606/200 |

(Continued)

FOREIGN PATENT DOCUMENTS

| EP | 0 364 420 A1 | 4/1990 | ............ A63M 29/00 |
| WO | WO 2006/127784 A2 | 11/2006 | |

OTHER PUBLICATIONS

International Search Report, Dated Dec. 15, 2009 for PCT/US2009/005642, (3-pgs).

*Primary Examiner* — Melanie Tyson
(74) *Attorney, Agent, or Firm* — Brinks Gilson & Lione (57) ABSTRACT

A dilator tip (100) for deploying and positioning an endovascular device (570) at a treatment site includes an elongate body (105) having at least two substantially longitudinal channels (110) in an outer surface (105s) of the body and at least two deployment struts (115). Each deployment strut (115) has a free end (120) releasably attached to a proximal edge (575) of an endovascular device (570) to be deployed, a constrained end (125) restrained within one of the longitudinal channels (110), and a pivot portion (130) between the free end (120) and the constrained end (125). In an undeployed configuration of the dilator tip (100), the free ends (120) reside within the longitudinal channels (110), and in a deployed configuration of the dilator tip (100), the free ends (120) are pivotally extended away from the longitudinal channels (110) by way of the pivot portions (130).

20 Claims, 5 Drawing Sheets

(56) References Cited

U.S. PATENT DOCUMENTS

| | | | |
|---|---|---|---|
| 6,540,722 B1 | 4/2003 | Boyle et al. | 604/106 |
| 7,150,756 B2 | 12/2006 | Levinson et al. | 606/200 |
| 7,556,646 B2 * | 7/2009 | Yang et al. | 623/2.11 |
| 2003/0153943 A1 | 8/2003 | Michael et al. | 606/200 |
| 2006/0089666 A1 | 4/2006 | Linder et al. | 606/200 |
| 2007/0142858 A1 | 6/2007 | Bates | 606/200 |

* cited by examiner

SYSTEM AND METHOD FOR DEPLOYING AND POSITIONING AN ENDOVASCULAR DEVICE

RELATED APPLICATION

The present patent document is the National Stage of International Application No. PCT/US2009/05642, filed Oct. 16, 2009, which claims the benefit of the filing date under 35 U.S.C. §119(e) of U.S. Provisional Patent Application Ser. No. 61/106,374, which was filed on Oct. 17, 2008, and is hereby incorporated by reference in its entirety.

TECHNICAL FIELD

The present disclosure is directed generally to endovascular devices and more particularly to a dilator tip, a system and a method for deploying and positioning an endovascular device at a treatment site in a body vessel.

BACKGROUND ART

If the strength or resilience of a blood vessel wall weakens or deteriorates, as may occur with aging or disease, the force of blood flow through the vessel may cause a portion of the wall to stretch or balloon outward, causing an aneurysm. If the aneurysm is left untreated, the vessel wall may further expand and ultimately rupture, often resulting in death.

To prevent rupturing of an aneurysm, an endoluminal graft may be introduced into a blood vessel and deployed to span the length of the aneurysmal sac, thereby providing a path for blood to flow past the aneurysm. Endovascular grafts (stent grafts or endografts) include a graft fabric secured to a cylindrical scaffolding or framework of one or more stents. The stent(s) provide rigidity and structure to hold the graft open in a tubular configuration as well as the outward radial force needed to create a seal between the graft and a healthy portion of the vessel wall. Blood flowing through the vessel is channeled through the hollow interior of the stent graft to reduce, if not eliminate, the stress on the vessel wall at the location of the aneurysm. Endografts reduce the risk of rupture of the blood vessel wall at the aneurysmal site and allow blood to flow through the vessel without interruption.

Aneurysms occurring in the aorta, the largest artery in the human body, may occur in the chest (thoracic aortic aneurysm) or in the abdomen (abdominal aortic aneurysm). Due to the curvature of the aortic arch, thoracic aortic aneurysms can be particularly challenging to treat. Other parts of the vasculature, such as the common iliac artery which extends from the aorta, may be extremely tortuous and may present various challenges when implanting an endograft.

Endograft delivery systems may include retention elements, such as trigger wires, intended to allow selective release and deployment of portions of the endograft once an overlying outer sheath is retracted. The release of the trigger wires may cause unintended longitudinal motion, however, which results in a shifting of a portion or the entirety of the endograft. Such motion may be particularly detrimental in a curved vessel. For example, instead of having a perpendicular orientation to blood flow, the proximal (leading) end of the stent graft may become tilted at an undesirable angle that makes the endograft susceptible to leakage. Longitudinal movement of the endograft could also result in the unintended blockage of one or more major branch arteries resulting in downstream ischaemia. An improved method of deploying and positioning endovascular devices is desirable.

DISCLOSURE OF THE INVENTION

An improved system and method for deploying and positioning an endovascular device in a body vessel have been developed. The system and method are preferably based on a channeled dilator tip that includes deployment struts. The system and method may be especially advantageous for placing endovascular devices (e.g., endografts) in the aortic anatomy, particularly in the thoracic aorta where radial curvature and tortuosity may otherwise hinder proper positioning of the devices. Using the system and method described herein, endovascular devices may be properly positioned and/or oriented during deployment so as to minimize blood leakage and prevent collapse.

The preferred dilator tip includes an elongate body having at least two substantially longitudinal channels in an outer surface of the body and at least two deployment struts. Each deployment strut has a free end releasably attached to a proximal edge of an endovascular device to be deployed, a constrained end restrained within one of the longitudinal channels, and a pivot portion between the free end and the constrained end. In an undeployed configuration of the dilator tip, the free ends reside within the longitudinal channels, and in a deployed configuration of the dilator tip, the free ends are pivotally extended away from the longitudinal channels by way of the pivot portions.

Preferably the free end and the constrained end of each deployment strut have a substantially longitudinal orientation in the undeployed configuration.

In an embodiment the longitudinal orientation comprises a fully open position of the pivot portion, an angle between the free end and the constrained end being nominally about 180°.

In an embodiment the longitudinal orientation comprises a fully closed position of the pivot portion, an angle between the free end and the constrained end being nominally about 0°.

Preferably the deployment struts comprise a shape memory material and are configured to have a memory of the longitudinal orientation.

The free end of each deployment strut may comprise a distal wire loop for releasable attachment to the proximal edge of the endovascular device.

The distal loop may form a closed coil or the distal loop may have an open structure.

Preferably the pivot portion of each deployment strut comprises a coiled portion of a wire joining the free end to the constrained end.

A portion of the outer surface of the elongate body may overly a proximal end of each longitudinal channel, thereby forming a ledge for constraining the constrained end of the deployment strut within the channel.

In the preferred embodiment the free ends of the deployment struts are located at their distal ends and the constrained ends of the deployment struts are located at their proximal ends.

Preferably, when pivotally extended away from the longitudinal channels, the free ends of the deployment struts are oriented at an obtuse angle with respect to the constrained ends.

In an embodiment the dilator tip includes three to eight longitudinal channels.

The preferred system includes an endovascular device in a delivery configuration and a delivery catheter radially adjacent to the endovascular device. The delivery catheter has a proximal dilator tip including an elongate body having at least two substantially longitudinal channels in an outer surface of the body and at least two deployment struts. Each deployment strut has a free end releasably attached to a proximal edge of the endovascular device, a constrained end restrained within one of the longitudinal channels, and a pivot portion between the free end and the constrained end. In an undeployed configuration of the dilator tip, the free ends reside within the longitudinal channels, and in a deployed configuration of the dilator tip, the free ends are pivotally extended away from the longitudinal channels by way of the pivot portions.

Embodiments of the system include a dilator tip as described above.

In an embodiment the free end of each deployment strut comprises a distal wire loop for releasable attachment to the proximal edge of the endovascular device.

Preferably there is provided a trigger wire having a distal end connected to a controller outside the body vessel and a proximal end releasably secured to the proximal edge of the endovascular device passing through or about the wire loop of each deployment strut to provide the releaseable attachment.

Preferably the trigger wire has a distal end connected to a controller.

The free end of each deployment strut may be releaseably attached to a proximal apex of a stent.

In an embodiment the stent is connected to a graft material, the endovascular device being a stent graft.

The ratio of deployment struts and channels to apices is 1:1 or less than 1:1.

In a preferred embodiment the free end and the constrained end of each deployment strut have a longitudinal orientation in the undeployed configuration, the longitudinal orientation comprising a fully closed position of the pivot portion, the angle between the free end and the constrained end being nominally about 0°; the deployment struts comprise a shape memory material and are configured to have a memory of the longitudinal orientation; a portion of the outer surface of the elongate body overlies a proximal end of each longitudinal channel, thereby forming a ledge for constraining the constrained end of the deployment strut within the channel; the pivot portion of each deployment strut comprises a coiled portion of a wire joining the free end to the constrained end; the endovascular device is a stent graft including a stent attached to a graft material; and the free end of each deployment strut comprises a distal loop, and a trigger wire having a proximal end releasably secured to a proximal apex of the stent passes through or about the loop of each deployment strut to provide the releasable attachment.

The preferred method includes providing a deployment system comprising an endovascular device in a delivery configuration and a delivery catheter radially adjacent to the endovascular device. The delivery catheter has a proximal dilator tip including an elongate body having at least two substantially longitudinal channels in an outer surface of the body and at least two deployment struts. Each deployment strut has a free end releasably attached to a proximal edge of the endovascular device, a constrained end restrained within one of the longitudinal channels, and a pivot portion between the free end and the constrained end. The method further includes advancing the deployment system to a treatment site in a body vessel and deploying the proximal edge of the endovascular device. The free end of each deployment strut is pivotally extended away from the longitudinal channel to contact the body vessel, and the constrained end of each deployment strut remains within the channel. Remaining portions of the endovascular device are deployed, while the free ends of the deployment struts restrain the proximal edge of the endovascular device from undesired motion. The free ends of the deployment struts are detached from the proximal edge of the endovascular device to allow the free ends to pivotally return to the longitudinal channels, and the delivery catheter including the proximal dilator tip is removed from the body vessel.

The deploying of the proximal edge and the deploying of the remaining portions of the endovascular device may comprise retracting a tubular sheath overlying the endovascular device.

During the deployment of the proximal edge of the endovascular device, the proximal edge may exert a sufficient outward radial force to compel the free ends of the deployment struts against the body vessel.

The method may further comprise, after deploying at least the proximal edge of the endovascular device and prior to detaching the free ends of the deployment struts from the proximal edge, advancing the dilator tip to adjust positioning of the endovascular device in the body vessel.

The method may further comprise, after deploying at least the proximal edge of the endovascular device and prior to detaching the free ends of the deployment struts from the proximal edge, retracting the dilator tip to adjust positioning of the endovascular device in the body vessel.

Detaching the free ends of the deployment struts from the proximal edge of the endovascular device may comprise releasing trigger wires connecting the free ends to the proximal edge of the endovascular device.

The deployment struts may comprise a shape memory alloy and the free ends may pivotally return to the longitudinal channels by a shape recovery process.

BRIEF DESCRIPTION OF THE DRAWINGS

Preferred embodiments of the present invention are now described, by way of example only, with reference to the accompanying drawings, in which.

DESCRIPTION OF THE PREFERRED EMBODIMENTS

Throughout the specification, the term "distal" refers to the end of an endovascular device or component, or to a part of the aorta, that is further away from the heart in the direction of blood flow through the aorta. The term "proximal" refers to the end of an endovascular device or component, or part of the aorta, that is nearer to the heart.

Figure 1A:
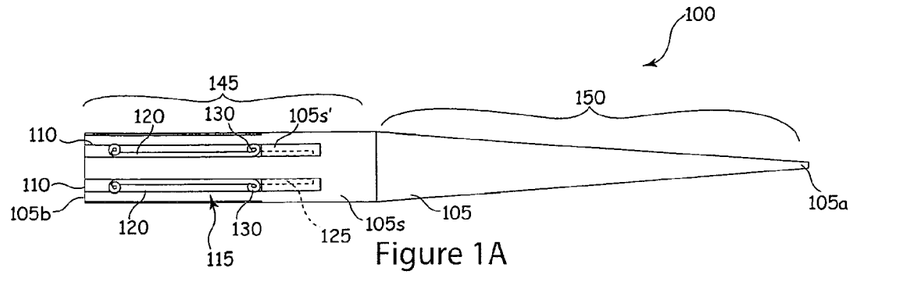
FIG. 1A shows a side view of an embodiment of a dilator tip of a delivery catheter in an undeployed configuration for passage into or out of a body vessel.
Figures 1B, 2A:
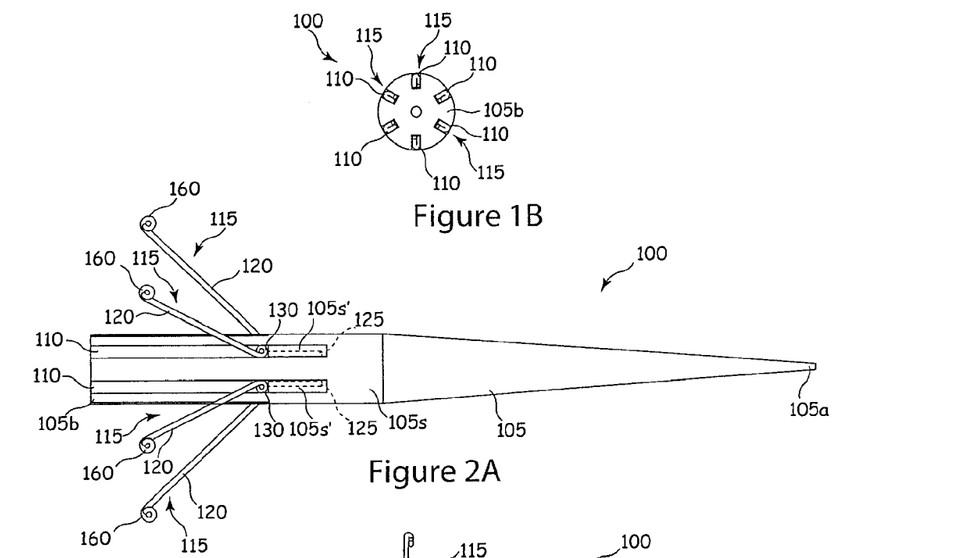
FIG. 1B shows a distal end view of the dilator tip of FIG. 1A.
FIG. 2A shows a side view of the dilator tip of FIG. 1A in a deployed configuration for use a body vessel.
Figure 2B:
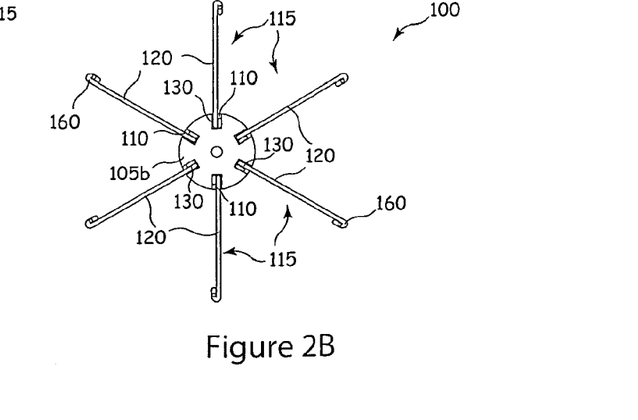
FIG. 2B shows a distal end view of the dilator tip of FIG. 2A.

FIGS. 1A-1B and 2A-2B show an embodiment of the dilator tip of a delivery catheter for delivering and deploying an endovascular device. FIG. 1A shows a side view of the dilator tip 100 in a collapsed or undeployed configuration for passage into or out of a body vessel, and FIG. 1B provides a distal end view of the dilator tip 100 of FIG. 1A. FIG. 2A shows a side view of the dilator tip 100 of the delivery catheter in a deployed configuration for use a body vessel, and FIG. 2B provides a distal end view of the dilator tip 100 of FIG. 2A.

The dilator tip 100 includes an elongate body 105 having a proximal end 105a and a distal end 105b. The distal end 105b includes at least two longitudinal channels 110 penetrating an outer surface 105s of the body 105. According to the embodiment shown in FIGS. 1A-2B, the dilator tip includes six longitudinal channels 110 symmetrically positioned about the circumference of the elongate body 105. It is also contemplated that the dilator tip 110 may include from three to eight longitudinal channels 110, such as four, five, or seven channels 110. Generally, the preferred number of longitudinal channels 110 is determined by the size of the endovascular device to be deployed, as discussed further below.

Referring to FIGS. 1A to 2B, each channel 110 is sized to contain a deployment strut 115 having a free end 120, a constrained end 125, and a pivot portion 130 between the free and constrained ends 120, 125. The pivot portion 130 may be a hinge, for example. The free end 120 is pivotally extendible away from the longitudinal channel 110 by way of the pivot portion 130 and is configured for detachable attachment to a proximal edge of an endovascular device, as will be discussed further below in reference to FIGS. 5A-5D and 6. When pivotally extended away from the longitudinal channel 110, as shown for example in FIGS. 2A and 3B, the free end 120 of the deployment strut 115 is preferably oriented at an obtuse angle with respect to the constrained end 125. In this orientation, the free end 120 of the deployment strut 115 can effectively engage the body vessel and aid in the deployment and placement of the endovascular device.

The constrained end 125 of the deployment strut 115 is restrained within the longitudinal channel 110. A ledge portion 105s' of the outer surface 105s of the elongate body 105 may overlie a proximal end of each of the longitudinal channels 110 to secure, or to aid in securing, the constrained end 125 within the channel 110. The constrained end 125 of the deployment strut 115 may also be restrained within the channel 110 by other or additional means. For example, the constrained end 125 may be press fit, adhesive bonded, moulded and/or otherwise secured within the longitudinal channel 110. The constrained end 125 may include a hook or other protrusion for engaging an inner surface of the elongate body 105 to improve the security of the restraint. Also or alternatively, the constrained end 125 of each strut 115 may be connected to a ring circumferentially embedded within the elongate body. It is also envisaged that the pivot portion 130 may be restrained within the longitudinal channel 110.

Referring again to FIG. 1A, the elongate body 105 may include a generally cylindrical distal portion 145 and a radially tapered (e.g., conical) proximal portion 150. The radially tapered shape of the proximal edge 150 is intended to facilitate smooth passage of the delivery system through the vasculature. It is also contemplated that the elongate body 105 may have a radially tapered or conical shape along an entire length thereof from the proximal end 105a to the distal end 105b.

Figure 3A:
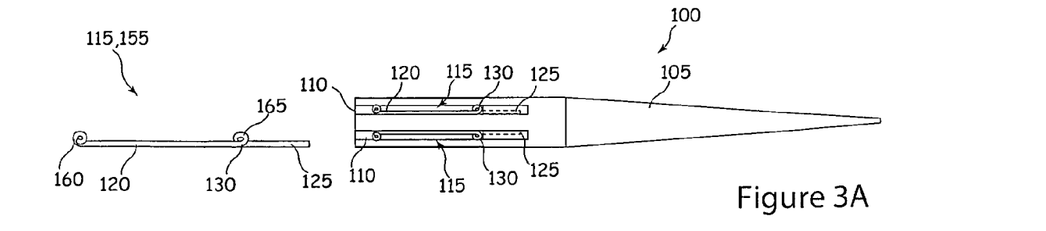
FIGS. 3A and 3D show a side view of an embodiment of a deployment strut having a free end and a constrained end in a longitudinal orientation and a side view of a dilator tip including the deployment strut.

Both the free end 120 and the constrained end 125 of the strut 115 adopt a longitudinal orientation for passage of the dilator tip 100 into and out of the body vessel. Referring to FIG. 3A, the longitudinal orientation 155 of the deployment strut 115 may include a fully open position of the pivot portion 130, where an angle between the free end 120 and the constrained end 125 is nominally about 180°. Alternatively, referring to FIG. 4A, the longitudinal orientation 255 of the deployment strut 215 may include a fully closed position of the pivot portion 230, where an angle between the free end 220 and the constrained end 225 is nominally about 0°. When the deployment struts 115, 215 are in the longitudinal orientation 155, 255, the delivery catheter including the dilator tip 100, 200 may be delivered into or removed from the body without damaging the vessel.

Figure 3B:
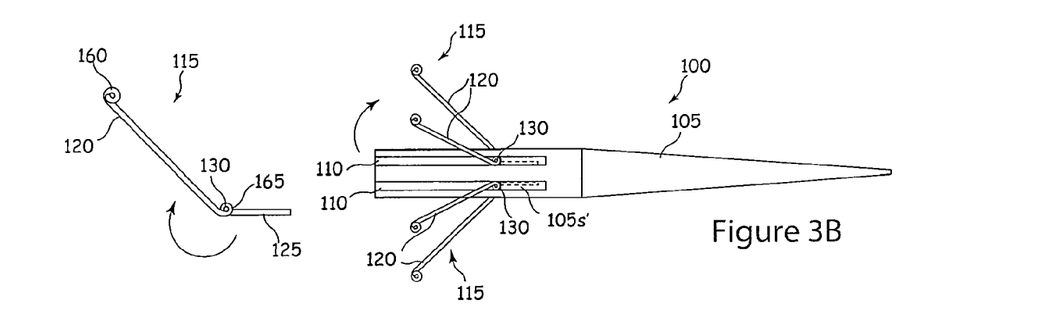
FIGS. 3B and 3C show a side view of an embodiment of a deployment strut having a free end in a pivotally extended configuration and a side view of a dilator tip including the deployment strut.
Figure 3C:
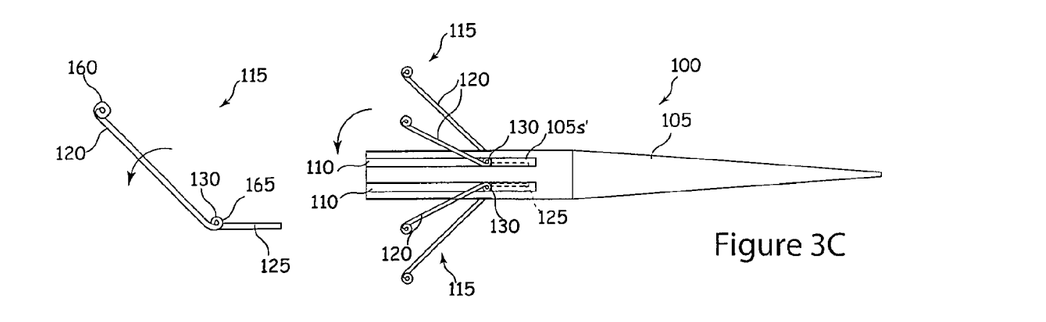
Figure 3D:
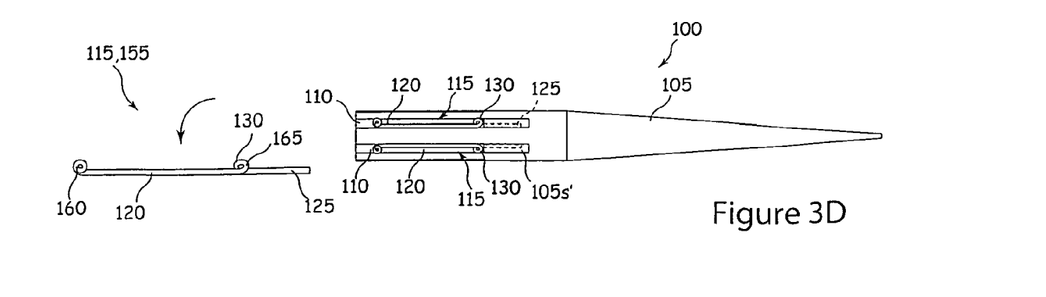

According to the embodiment of FIG. 3A, in which the longitudinal orientation 155 includes a fully open position of the pivot portion 130, the free end 120 of the deployment strut 115 pivotally extends away from the longitudinal channel 110 and toward the constrained end 125, as shown in FIG. 3B, for deployment and placement of the endovascular device. Accordingly, the pivot portion 130 of the deployment strut 115 is situated near the proximal end of the longitudinal channel 110 to ensure that the free end 120 of the deployment strut 115 is supported within the channel 110 in the longitudinal orientation 155. Following deployment of the endovascular device, the pivotally extended deployment strut 115 may return to the longitudinal orientation 155, as shown in FIGS. 3C and 3D, by passing through an acute angle with respect to the longitudinal channel 110.

Figure 4A:
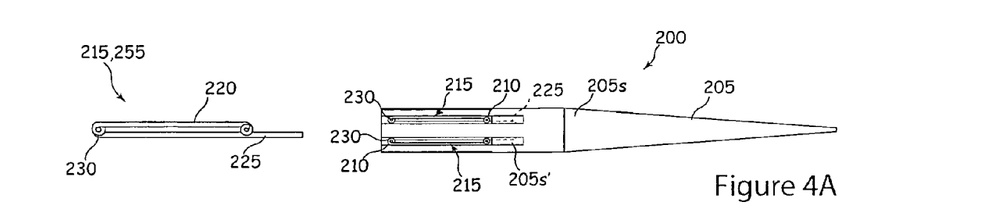
FIGS. 4A and 4D show a side view of an embodiment of a deployment strut having a free end and constrained end in a longitudinal orientation and a side view of a dilator tip including the deployment strut.
Figure 4B:
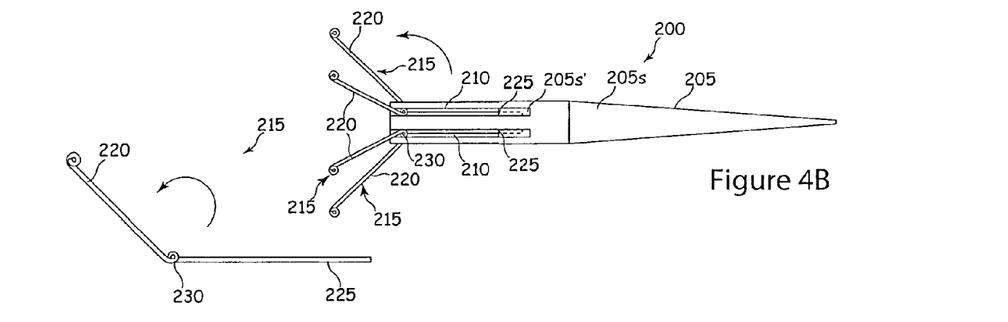
FIGS. 4B and 4C show a side view of an embodiment of a deployment strut having a free end in a pivotally extended configuration and a side view of a dilator tip including the deployment strut.
Figure 4C:
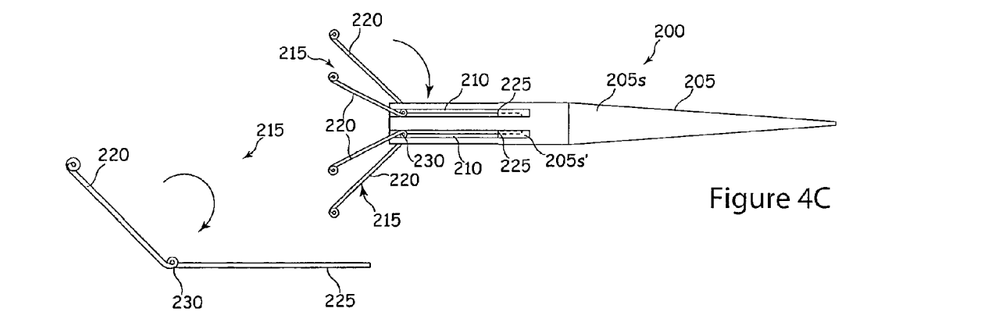
Figure 4D:
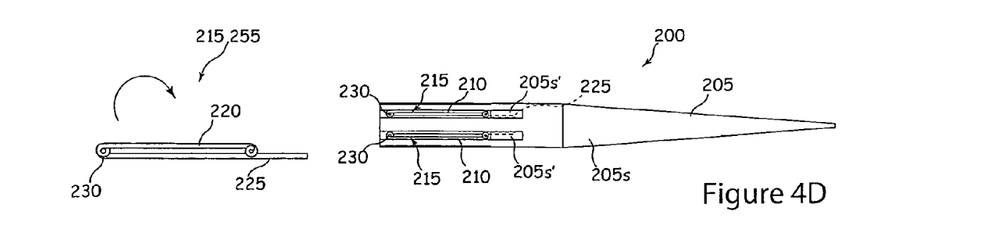

In the embodiment of FIG. 4A, in which the longitudinal orientation 255 includes a fully closed position of the pivot portion 230, the free end 220 of the deployment strut 215 pivotally extends away from both the longitudinal channel 210 and the constrained end 225 of the deployment strut 215, as shown in FIG. 4B, for deployment and positioning of the endovascular device. Accordingly, the pivot portion 230 of the deployment strut is situated near the distal end of the longitudinal channel 210 to ensure that the free end 220 is free to pivot outward from the closed position. The constrained end 225 of the strut 215 has a longer length than the deployment strut 115 of FIGS. 3A-3B since it spans both the exposed and covered portions of the longitudinal channel 210. (The covered portion of the channel 210 underlies the ledge portion 205s' which was discussed above in reference to FIG. 1A.) After the endovascular device is deployed, the pivotally extended deployment strut 215 may return to the longitudinal orientation 255 by passing through an obtuse angle with respect to the longitudinal channel 210 and the constrained end 225 of the strut 215.

Referring again to FIGS. 2A-2B, the free ends 120 of the deployment struts 115 may include a distal wire loop 160 that may be releasably attached to the proximal edge of the endovascular device. As used herein, "releasably attached," "detachably attached," "releasably secured," "releasably connected," and variants such as "detachable attachment" and "releasable connection" and others, refer to temporary bindings of one component to another that may be deliberately released, detached or severed during use. The distal wire loop 160 of the free end 120 of the deployment strut 115 preferably forms a closed or complete coil, but it is also contemplated that the distal wire loop 160 may have an open structure, such as that of a hook or anchor. As discussed further below in reference to FIG. 6, a trigger wire 595 passing through or wrapping around the distal wire loop 160 of the deployment strut 115 may provide the means of detachable attachment to the proximal edge 575 of the device 570.

The pivot portion 130 of the deployment strut 115 may include a central coil 165 that joins the free end 120 to the constrained end 125. Inclusion of the central coil 165 is expected to reduce peak strain in the pivot portion 130 of the deployment strut 115 during pivotal extension of the free end 120, isolate the bending of the strut 115 to the central coil 165, and allow adequate spring-back to the longitudinal orientation.

FIGS. 5A-5D illustrate steps of a method of deploying an endovascular device at a treatment site in a body vessel. The method entails providing a delivery system 500 including (a) an endovascular device 570 in a delivery configuration and (b) a delivery catheter radially adjacent to the endovascular device 570, where the delivery catheter includes a proximal dilator tip 100 having an elongate body 105 disposed proximally adjacent to the endovascular device 570. The elongate body 105 has a distal end 105b including at least two longitudinal channels 110 in an outer surface 105s of the body 105. Each channel 110 is sized to contain a deployment strut 115 having a free end 120, a constrained end 125, and a pivot portion 130 therebetween, as shown in FIGS. 1A-2B.

Figure 5A:
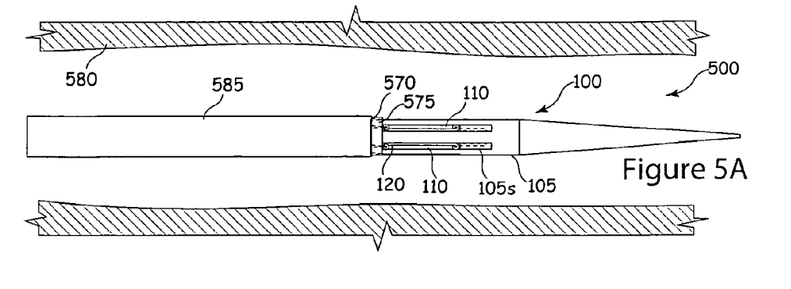
FIGS. 5A-5D show a method of deploying an endovascular graft at a treatment site in a body vessel utilizing the dilator tip of FIGS. 1A-2D.
Figure 5B:
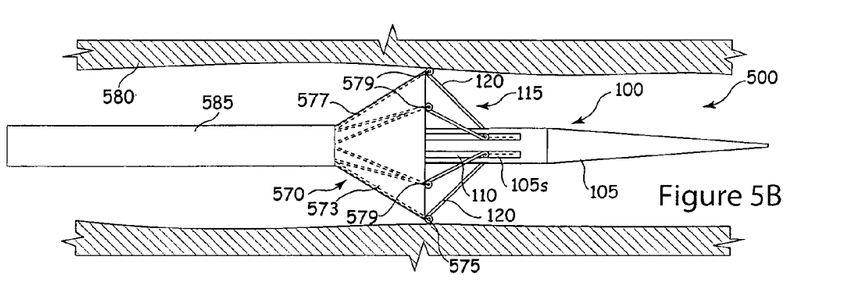
Figure 5C:
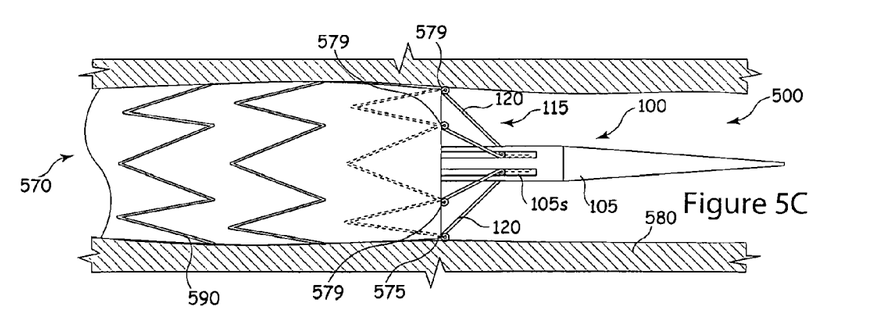

Referring to FIGS. 5B and 5C, the free ends 120 of the deployment struts 115 are detachably attached to a proximal edge 575 of the endovascular device 570, which, according to this example, is an endovascular graft 570 including a graft material 573 secured to at least one stent 577. According to this embodiment, the free ends 120 of the deployment struts 115 are detachably attached to proximal apices 579 of the stent 577, which are positioned at or near the proximal edge 575 of the endograft 570. The free end 120 may also be detachably attached to the graft material 573 near the proximal apices 579 of the stent 577. Alternatively, the free end 120 is not detachably attached to the graft material 573, but only to the stent 577. The detachable attachment of the free ends 120 of the deployment struts 115 to the proximal edge 575 of the endovascular device 570 is discussed further below in reference to FIG. 6.

Referring again to FIG. 5A, the delivery system 500 is advanced to a treatment site in a body vessel 580. An exemplary deployment procedure may include insertion of the delivery system into a small incision in the groin to access the patient's femoral artery. The delivery system can be directed under fluoroscopic guidance to a weakened or damaged section of the thoracic aorta or to another portion of the vasculature.

As shown in FIG. 5B, the proximal edge 575 of the endovascular device 570 is deployed, and the free end 120 of each deployment strut 115 is pivotally extended away from the longitudinal channel 110. The constrained end 125 of each deployment strut 115 remains within the channel 110. A tubular sheath 585 overlying the device 570 may be retracted to effect the deployment, thereby allowing the proximal edge 575 to self-expand radially to contact the body vessel 580. The device 570 may include one or more components (e.g., the stent 577) made of a nickel-titanium alloy or other shape memory material that deploys superelastically upon removal of a restraining force (such as that supplied by the tubular sheath 585). During deployment, the self-expanding proximal edge 575 of the device 570 (i.e., a proximal portion of the stent 577) exerts a sufficient outward radial force to compel the free ends 120 of the deployment struts 115 against the body vessel 580.

Referring to FIG. 5C, remaining portions 590 of the endovascular device 570 are deployed to contact the body vessel 585. For example, the tubular sheath 585 may be retracted to permit gradual self-expansion of the remaining portions 590. The deployment struts 115 that have been forced against the body vessel 585 help to maintain proper placement of the proximal edge 575 of the endovascular device 570 as the remaining portions 590 radially expand. The constant length of each deployment strut 115 can assist in aligning the proximal edge 575 of the endovascular device 570 and preventing unwanted distal or proximal movement.

Figure 5D:
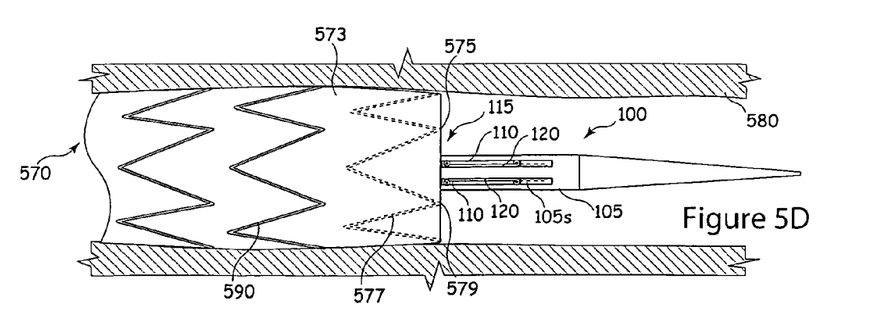

In FIG. 5D, the free end 120 of each deployment strut 115 is released from the proximal edge 575 of the endovascular device 570. The free ends 120 thus pivotally return to the longitudinal channels 110 and assume a longitudinal orientation 155 (e.g., as shown in FIG. 3A) suitable for transport through the vessel 580. The dilator tip 100 may then be removed from the body vessel 580. The deployment struts 115 may be advantageously made of a shape memory material configured to "remember" the longitudinal orientation 155, as discussed above. Accordingly, the free ends 120 may pivotally return to the longitudinal channels 110 by a shape recovery process once released from the proximal edge 575. Since the shape memory effect is generally one-way, the free ends 120 may automatically return to the longitudinal orientation 155, but they do not spontaneously extend (pivot outward). Instead, as discussed above, they are forced outward by the self-expansion of the proximal edge 575 of the endovascular device 570 during the deployment process.

Figure 6:
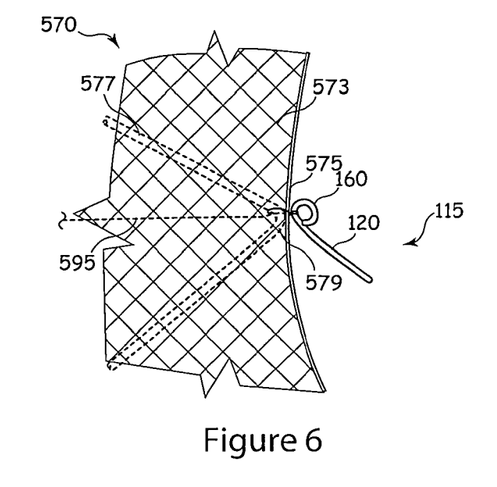
FIG. 6 shows a close-up view of a proximal edge of an endovascular graft and a free end of a deployment strut, the free end being releasably attached to the proximal edge.

Referring to FIG. 6, detaching the free end 120 of each deployment strut 115 from the proximal edge 575 of the endovascular device 570 may entail releasing a trigger wire or suture 595 connecting the free end 120 to the proximal edge 575. According to the example of FIG. 6, which provides a close-up view of an exemplary endovascular device 570 attached to the free end 120 of a deployment strut 115, the endovascular device is an endograft 570 including a graft material 573 attached to one or more stents 577. The trigger wire 595 has a first end releasably secured (e.g., by wrapping or winding) to both a proximal apex 579 of the stent 577 and the free end 120 of the deployment strut 115. The proximal apex 579 is situated at or near the proximal edge 575 of the endograft 570 and may correspond to, for example, a junction of two stent struts or to a bend in a stent wire. A second end of the trigger wire 595 extends outside the body vessel to a controller for manipulation by a clinician. When the endograft 570 is deployed, the outward radial force exerted by the expanding stent 577 can be transmitted to the deployment struts 115 due to the connection between the stent 577 and the struts 115 provided by the trigger wire 595. Once the radially expanded device 570 is suitably situated in the vessel 580, a clinician may pull on the trigger wire via the controller outside the body vessel to release the wire from the apex 579 of the stent 577 and withdraw it from the wire loop 160 of the deployment strut 115. The connection between the free end 120 of the deployment strut 115 and the proximal edge 575 of the endograft 570 may thus be severed, freeing the deployment strut 115 to return to its longitudinal orientation 155. In another embodiment, the free ends 120 of the deployment struts 115 engage eyelets or other recesses on the stent 577.

An advantage of employing a delivery system including the present dilator tip to deploy and position an endovascular device in a body vessel is that the placement of the device may be adjusted after deployment. Conventional deployment systems and methods generally do not permit repositioning of a device once it is deployed. Prior to detaching the free end of each deployment strut from the proximal edge of the endovascular device, the dilator tip may be advanced or retracted to adjust the orientation of the proximal edge or the positioning of the entire endovascular device. The deployment struts have sufficient stiffness to push the proximal edge of the endovascular device in a distal direction without buckling, and sharp curves in the vessel can be negotiated.

The number of deployment struts 115 and longitudinal channels 110 positioned about the circumference of the dilator tip 100 is generally determined by the size of the endovascular device (e.g., endograft) to be deployed. Generally, larger diameter endografts may include stents having a larger number of "points" or "apices" compared to smaller diameter (or smaller French) endografts. The number of deployment struts and, consequently, the number of longitudinal channels of the dilator tip may advantageously have a 1:1 correspondence with the number of apices or points of the stent. For example, a six-point zigzag stent having six apices, similar to the stents 577 shown in FIGS. 5A-5D, may be successfully deployed and placed with a dilator tip that includes six channels and six deployment struts (1:1 ratio of struts/channels to apices). Generally speaking, an endograft that radially expands to a larger diameter may be deployed using a dilator tip with a greater number of longitudinal channels and a correspondingly greater number of deployment struts.

While a 1:1 ratio of struts/channels to apices is believed to be beneficial for device placement, it may be advantageous to reduce the number of channels and deployment struts, thereby minimizing the profile of the delivery system. Accordingly, the ratio between the number of deployment struts and the apices of the stent may be less than 1:1, such as, 1:2 or 1:3. In a specific example, it is contemplated that the six-point zigzag stent described above may be successfully deployed and positioned with a dilator tip including three channels and three deployment struts (1:2 ratio of struts/channels to apices) or two channels and two deployment struts (1:3 ratio of struts/channels to apices).

Figure 7:
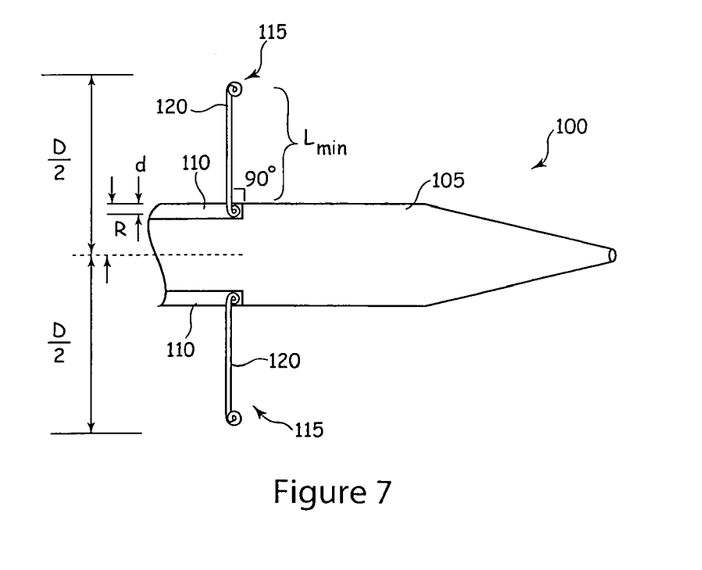
FIG. 7 is a schematic showing the geometry assumed in calculating a minimum length of the free ends of the deployment struts in an embodiment.

The size of the endovascular device also determines the desired length of the deployment struts. The preferred minimum length of the free end of the deployment struts for particular endovascular device diameters may be calculated according to a geometric relationship. Referring to FIG. 7, the relationship is:

$$\frac{D}{2} - (R - d) = L_{min}$$

where D/2 represents the radius of the deployed endovascular device (e.g., endograft); R represents the radius of the distal end of the dilator tip 100; where d represents the depth of the longitudinal channel 110; and $L_{min}$ represents the preferred minimum length of the free end 120 of the deployment struts 115. The minimum length corresponds to a 90° degree angle between the free end of the deployment strut and the channel. In general, a preferred length $L_{pref}$ of the free end 120 of the strut 115 is longer than the minimum length ($L_{pref} > L_{min}$). The preferred minimum length $L_{min}$ of the struts 115 may be in the range of from about 5 mm to about 25 mm, for example, or from about 10 mm to about 20 mm, depending on the dimensions of the delivery system and the endovascular device.

Due to the desire to maintain a low profile of the delivery system for transport through the vessel, it is desirable to minimize the thickness of the deployment struts without detrimentally reducing their stiffness. For example, suitable deployment struts may have a thickness of from about 0.1 mm to about 1.0 mm. The struts may be formed from a round wire having a substantially circular cross-section or from a flat wire having a square or rectangular cross-section. As discussed above, the deployment struts 115 may be secured within the longitudinal channels 110 of the dilator tip 100 by way of the ledge portion 105s' of the elongate body 105 (e.g., see FIG. 1A) and/or by press fitting, adhesive bonding, moulding or other means.

The dilator tip including the two or more longitudinal channels may be made of a biocompatible material, such as one or more biocompatible polymers. Suitable biocompatible polymers may include, for example, a polyamide (e.g., nylon), thermoplastic fluorocarbon (e.g., fluoroethylene-propylene (FEP)), polyether block amide (PEBA), polyolefin, polyimide, polyurethane, or polyvinyl chloride (PVC). The tip may be fabricated by extrusion, moulding and/or forming processes known in the art.

The deployment struts may be made of biocompatible materials, preferably biocompatible metals or alloys that may be drawn into wires or laser cut to the appropriate dimensions. Advantageously, the deployment struts may be formed of a shape memory material and may be configured to "remember" and return to the longitudinal orientation after deployment of the endovascular device. Shape memory polymers or other shape memory alloys may also be suitable for the deployment struts. Alternatively, the deployment struts may be formed of a resilient material having sufficient elasticity to spring back to the longitudinal orientation after the endovascular device is deployed. Preferably, the deployment struts are formed of a superelastic nickel-titanium alloy and undergo a heat-setting treatment before use to impart a memory of the longitudinal orientation, as is discussed in greater detail below.

The shape memory (or superelastic) material of the deployment struts may be an equiatomic or a near-equiatomic nickel-titanium alloy, such as Nitinol, which undergoes a reversible phase transformation between a martensitic phase and an austenitic phase that allows a previous configuration to be "remembered" and recovered. For example, strain imparted to a component to achieve a pivotally expanded deployment configuration while martensitic may be substantially recovered during a reverse phase transformation to austenite, such that the component reverts to a "remembered" configuration (e.g., the longitudinal orientation) when the stress is released. Typically, recoverable strains of about 8-10% may be obtained from superelastic nickel-titanium alloys.

As generally understood by those skilled in the art, martensite start temperature ($M_s$) refers to the temperature at which a phase transformation to martensite begins upon cooling for a nickel-titanium shape memory alloy, and martensite finish temperature ($M_f$) refers to the temperature at which the phase transformation to martensite concludes. Austenite start temperature ($A_s$) refers to the temperature at which a phase transformation to austenite begins upon heating for a nickel-titanium shape memory alloy, and austenite finish temperature ($A_f$) refers to the temperature at which the phase transformation to austenite concludes.

Values of $A_f$ at or below body temperature (37° C.) are generally preferred for the superelastic nickel-titanium alloys of the deployment struts. Slightly nickel-rich Nitinol alloys including, for example, about 51 at. % Ni and about 49 at. % Ti are known to be useful for medical devices which are superelastic at body temperature. In particular, alloys including 50.6-50.8 at. % Ni and 49.2-49.4 at. % Ti are considered to be medical grade Nitinol alloys and are suitable for the present deployment struts. The nickel-titanium alloy may further include one or more additional alloying elements that substitute for one or both of the nickel and titanium atoms. Suitable nickel-titanium alloys may be obtained from any of a number of commercial sources.

The nickel-titanium alloys may be cold worked into desired shapes (e.g., wires or tubes) by, for example, drawing, rolling, or another forming method. The cold working typically involves several forming passes in combination with interpass annealing treatments at temperatures in the range of from about 600° C. to about 800° C. The interpass annealing treatments soften the material between cold work passes, which typically impart 30-40% deformation to the material. Machining operations, such as, for example, drilling, cylindrical centerless grinding, or laser cutting may also be employed to fabricate the deployment struts.

A heat setting treatment may be employed to impart a "memory" of a desired high temperature shape and to optimize the shape memory/superelastic and mechanical properties of the deployment struts. The number, duration and the temperature of the heat setting treatments can affect the transformation temperatures. Typically, heat setting treatment temperatures of 400° C. to 550° C. are appropriate to set the final shape of the deployment struts and to optimize the properties.

An improved system and method for deploying and positioning an endovascular device in a body vessel have been described. The system and method utilize a channeled dilator tip with deployment struts. The system and method may be especially advantageous for placing endovascular devices (e.g., endografts) in the aortic anatomy, particularly in the thoracic aorta where radial curvature and tortuosity may otherwise hinder proper positioning of the devices. Using the system and method described herein, endovascular devices may be properly positioned and/or oriented during deployment so as to minimize blood leakage and prevent collapse.

Although the present invention has been described in considerable detail with reference to certain embodiments thereof, other embodiments are possible without departing from the present invention. The scope of the appended claims should not be limited, therefore, to the description of the preferred embodiments contained herein. All embodiments that come within the meaning of the claims are intended to be embraced therein. Furthermore, the advantages described above are not necessarily the only advantages of the invention, and it is not necessarily expected that all of the described advantages will be achieved with every embodiment of the invention.

The disclosures in U.S. 61/106,374, from which the present application claims priority, and in the accompanying abstract are incorporated herein by reference.

The invention claimed is:

1. A dilator tip for deploying and positioning an endovascular device at a treatment site in a body vessel, including:
    an elongate body including at least two substantially longitudinal channels in an outer surface of the body;
    at least two deployment struts, each deployment strut having a free end comprising a distal loop for releaseable attachment to a proximal edge of an endovascular device to be deployed, a constrained end restrained within one of the longitudinal channels, and a pivot portion between the free end and the constrained end;
    where, in an undeployed configuration of the dilator tip, the free ends reside within the longitudinal channels, and
    where, in a deployed configuration of the dilator tip, the free ends are pivotally extended away from the longitudinal channels by way of the pivot portions.

2. The dilator tip of claim 1, wherein the free end and the constrained end of each deployment strut have a substantially longitudinal orientation in the undeployed configuration.

3. The dilator tip of claim 2, wherein the longitudinal orientation comprises a fully open position of the pivot portion, the angle between the free end and the constrained end being nominally about 180°.

4. The dilator tip of claim 2, wherein the longitudinal orientation comprises a fully closed position of the pivot portion, the angle between the free end and the constrained end being nominally about 0°.

5. The dilator tip of claim 2, wherein the deployment struts comprise a shape memory material and are configured to have a memory of the longitudinal orientation.

6. The dilator tip of claim 1, wherein the distal loop forms a closed coil.

7. The dilator tip of claim 1, wherein the distal loop has an open structure.

8. The dilator tip of claim 1, wherein the pivot portion of each deployment strut comprises a coiled portion of a wire joining the free end to the constrained end.

9. The dilator tip of claim 1, wherein a portion of the outer surface of the elongate body overlies a proximal end of each longitudinal channel, thereby forming a ledge for constraining the constrained end of the deployment strut within the channel.

10. The dilator tip of claim 1, wherein the free ends of the deployment struts are located at distal ends thereof and wherein the constrained ends of the deployment struts are located at proximal ends thereof.

11. The dilator tip of claim 1, wherein, when pivotally extended away from the longitudinal channels, the free ends of the deployment struts are oriented at an obtuse angle with respect to the constrained ends.

12. The dilator tip of claim 1, including three to eight longitudinal channels.

13. A system for deploying and positioning an endovascular device at a treatment site in a body vessel, including:
    an endovascular device in a delivery configuration; and
    a delivery catheter radially adjacent the endovascular device, the delivery catheter including a proximal dilator tip comprising:
        an elongate body including at least two substantially longitudinal channels in an outer surface of the body;
        at least two deployment struts, each deployment strut having a free end including a distal loop for releaseable attachment to a proximal edge of an endovascular device to be deployed, a constrained end restrained within one of the longitudinal channels, and a pivot portion between the free end and the constrained end;
        where, in an undeployed configuration of the dilator tip, the free ends reside within the longitudinal channels, and
        where, in a deployed configuration of the dilator tip, the free ends are pivotally extended away from the longitudinal channels by way of the pivot portions.

14. The system of claim 13, wherein a trigger wire having a proximal end releasably secured to the proximal edge of the endovascular device passes through or about the loop of each deployment strut to provide the releaseable attachment.

15. The system of claim 14, wherein the trigger wire has a distal end connected to a controller.

16. The system of claim 14, wherein the distal loop at the free end of each deployment strut is releaseably attached to a proximal apex of a stent.

17. The system of claim 16, wherein the stent is connected to a graft material, the endovascular device being a stent graft.

18. The system of claim 16, wherein the ratio of deployment struts and channels to apices is 1:1.

19. The system of claim 16, wherein the ratio of deployment struts and channels to apices is less than 1:1.

20. The system of claim 13, wherein the free end and the constrained end of each deployment strut have a longitudinal orientation in the undeployed configuration, the longitudinal orientation comprising a fully closed position of the pivot portion, the angle between the free end and the constrained end being nominally about 0°;
- wherein the deployment struts comprise a shape memory material and are configured to have a memory of the longitudinal orientation;
- wherein a portion of the outer surface of the elongate body overlies a proximal end of each longitudinal channel, thereby forming a ledge for constraining the constrained end of the deployment strut within the channel;
- wherein the pivot portion of each deployment strut comprises a coiled portion of a wire joining the free end to the constrained end;
- wherein the endovascular device is a stent graft including a stent attached to a graft material;
- wherein a trigger wire having a proximal end releaseably secured to a proximal apex of the stent passes through or about the distal loop of each deployment strut to provide the releasable attachment.

* * * * *